US012751972B2

(12) United States Patent
Luo et al.

(10) Patent No.: US 12,751,972 B2
(45) Date of Patent: Oct. 6, 2026

(54) ANTI-CLAUDIN18.2 ANTIGEN-BINDING FRAGMENT OR ANTIBODY, AND USE THEREOF18255119

(71) Applicant: GUANGZHOU BIO-GENE TECHNOLOGY CO., LTD, Guangdong (CN)

(72) Inventors: Min Luo, Guangdong (CN); Guangchao Li, Guangdong (CN); Wen Ding, Guangdong (CN); Zhao Zhou, Guangdong (CN); Xuejun Wang, Guangdong (CN)

(73) Assignee: GUANGZHOU BIO-GENE TECHNOLOGY CO., LTD, Guangdong (CN)

( * ) Notice: Subject to any disclaimer, the term of this patent is extended or adjusted under 35 U.S.C. 154(b) by 660 days.

(21) Appl. No.: 18/039,678

(22) PCT Filed: Dec. 22, 2020

(86) PCT No.: PCT/CN2020/138240
§ 371 (c)(1),
(2) Date: May 31, 2023

(87) PCT Pub. No.: WO2022/126687
PCT Pub. Date: Jun. 23, 2022

(65) Prior Publication Data

US 2024/0050472 A1 Feb. 15, 2024

(30) Foreign Application Priority Data

Dec. 16, 2020 (CN) ......................... 202011486494.0

(51) Int. Cl.

| | |
|---|---|
| ***A61K 39/395*** | (2006.01) |
| ***A61K 35/17*** | (2015.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61P 35/00*** | (2006.01) |
| ***C07K 16/28*** | (2006.01) |
| ***C12N 5/0783*** | (2010.01) |

(52) U.S. Cl.
CPC .......... *A61K 35/17* (2013.01); *A61K 39/3955* (2013.01); *A61K 40/11* (2025.01); *A61K 40/31* (2025.01); *A61K 40/4202* (2025.01); *A61K 45/06* (2013.01); *A61P 35/00* (2018.01); *C07K 16/28* (2013.01); *C12N 5/0636* (2013.01); *A61K 2239/13* (2023.05); *A61K 2239/17* (2023.05); *A61K 2239/21* (2023.05)

(58) Field of Classification Search
CPC ............................ A61K 39/3955; C07K 16/28
See application file for complete search history.

(56) References Cited

U.S. PATENT DOCUMENTS

| | | | | |
|---|---|---|---|---|
| 10,421,817 | B1 * | 9/2019 | Hu | A61K 31/282 |
| 2021/0261658 | A1 | 8/2021 | Wu et al. | |
| 2022/0033491 | A1 | 2/2022 | Li et al. | |
| 2022/0185881 | A1 | 6/2022 | Yang et al. | |
| 2022/0235128 | A1 | 7/2022 | Qu et al. | |
| 2022/0411492 | A1 | 12/2022 | Yang et al. | |

FOREIGN PATENT DOCUMENTS

| | | | | |
|---|---|---|---|---|
| CN | 104877032 A | 9/2015 | | |
| CN | 109206524 A | 1/2019 | | |
| CN | 109762067 A | 5/2019 | | |
| CN | 110606891 A | * 12/2019 | | A61K 35/00 |
| CN | 110857322 A | 3/2020 | | |
| CN | 111944048 A | 11/2020 | | |
| CN | 114634566 A | 6/2022 | | |
| WO | WO-2019173420 A1 | * 9/2019 | | G01N 33/57492 |
| WO | WO2020063988 A1 | 4/2020 | | |
| WO | WO2020200196 A1 | 10/2020 | | |
| WO | WO2020228806 A1 | 11/2020 | | |
| WO | WO2022126687 A1 | 6/2022 | | |

OTHER PUBLICATIONS

Chen, S., et al., "Advances in the Application of Claudins to Tumor Therapy", Chinese Journal of Biotechnology, claudin, vol. 35, No. 6, Jun. 25, 2019, pp. 931-941. (Translation).

Jiang, H. et al. "Claudin 18.2-Specific Chimeric Antigen Receptor Engineered T Cells for the Treatment of Gastric Cancer", JNCI J Natl Cancer Inst, vol. 111, No. 4, Apr. 30, 2019, pp. 409-418.

Sahin, U., et al., "First-in-human study of IMAB362, an anti-claudin 18.2 monoclonal antibody, in patients with advanced gastroesophageal cancer", Annals of Oncology, vol. 28, No. 5, Sep. 30, 2017, pp. 224-225.

International Search Report and Written Opinion received in PCT Application No. PCT/CN2020/138240 mailed on Sep. 15, 2021, 18 pages. (Translation).

(Continued)

*Primary Examiner* — Xiaozhen Xie
(74) *Attorney, Agent, or Firm* — Jenkins, Taylor & Hunt, P.A.

(57) ABSTRACT

Provided are an anti-Claudin 18.2 antigen-binding fragment or antibody, and the use thereof. CDR3 of a heavy chain variable region of the antigen-binding fragment comprises an amino acid sequence shown in SEQ ID NO. 3. CDR3 of a light chain variable region of the antigen-binding fragment comprises an amino acid sequence shown in SEQ ID NO. 6. The provided antigen-binding fragment and anti-Claudin 18.2 antibody can specifically bind to a variety of sources of Claudin 18.2 proteins, have no binding effect on other proteins, and have a high specificity. In addition, a chimeric antigen receptor and a CAR-T cell prepared by means of the antibody have obvious cytotoxicity on cells stably expressing the Claudin 18.2 protein.

10 Claims, 5 Drawing Sheets

Specification includes a Sequence Listing.

(56) References Cited

OTHER PUBLICATIONS

Office Action and Search received in Chinese Patent Application No. 202011486494.0 mailed on Mar. 17, 2023, 6 pages. (Translation).
International Preliminary Report on Patentability received in PCT Application No. PCT/CN2020/138240 mailed on Jun. 29, 2023, 11 pages. (Translation).
Notice of Grant received in Chinese Patent Application No. 202011486494.0 mailed on Aug. 25, 2023, 4 pages. (Translation).

* cited by examiner

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial sequence
<220> FEATURE:
<223> OTHER INFORMATION: CDR1 of the heavy chain variable region

<400> SEQUENCE: 1

Gly Tyr Thr Phe Thr Ser Tyr Val Met His
1               5                   10


<210> SEQ ID NO 2
<211> LENGTH: 10
<212> TYPE: PRT
<213> ORGANISM: Artificial sequence
<220> FEATURE:
<223> OTHER INFORMATION: CDR2 of the light chain variable region

<400> SEQUENCE: 2

Tyr Ile Asn Pro Tyr Asn Asp Gly Thr Lys
1               5                   10


<210> SEQ ID NO 3
<211> LENGTH: 10
<212> TYPE: PRT
<213> ORGANISM: Artificial sequence
<220> FEATURE:
<223> OTHER INFORMATION: CDR3 of the heavy chain variable region

<400> SEQUENCE: 3

Arg Gly Tyr Tyr Gly Pro Tyr Phe Asp Tyr
1               5                   10


<210> SEQ ID NO 4
<211> LENGTH: 17
<212> TYPE: PRT
<213> ORGANISM: Artificial sequence
<220> FEATURE:
<223> OTHER INFORMATION: CDR1 of the light chain variable region

<400> SEQUENCE: 4

Lys Ser Ser Gln Ser Leu Leu Asn Gly Gly Asn Gln Lys Asn Tyr Leu
1               5                   10                  15

Thr


<210> SEQ ID NO 5
<211> LENGTH: 7
<212> TYPE: PRT
<213> ORGANISM: Artificial sequence
```

<220> FEATURE:
<223> OTHER INFORMATION: CDR2 of the light chain variable region

<400> SEQUENCE: 5

Trp Ala Ser Thr Arg Glu Ser
1 5

<210> SEQ ID NO 6
<211> LENGTH: 9
<212> TYPE: PRT
<213> ORGANISM: Artificial sequence
<220> FEATURE:
<223> OTHER INFORMATION: CDR3 of the light chain variable region

<400> SEQUENCE: 6

Gln Asn Asp Tyr Tyr Tyr Pro Tyr Thr
1 5

<210> SEQ ID NO 7
<211> LENGTH: 119
<212> TYPE: PRT
<213> ORGANISM: Artificial sequence
<220> FEATURE:
<223> OTHER INFORMATION: the heavy chain variable region of the anti-Claudin 18.2 antibody

<400> SEQUENCE: 7

Gln Val Gln Leu Lys Gln Ser Gly Pro Glu Leu Val Lys Pro Gly Ala
1 5 10 15

Ser Val Lys Met Ser Cys Lys Ala Ser Gly Tyr Thr Phe Thr Ser Tyr
20 25 30

Val Met His Trp Val Lys Gln Lys Pro Gly Gln Gly Leu Glu Trp Ile
35 40 45

Gly Tyr Ile Asn Pro Tyr Asn Asp Gly Thr Lys Tyr Asn Glu Lys Phe
50 55 60

Lys Gly Lys Ala Thr Leu Thr Ser Asp Lys Ser Ser Ser Thr Ala Tyr
65 70 75 80

Met Glu Leu Ser Ser Leu Thr Ser Glu Asp Ser Ala Val Tyr Tyr Cys
85 90 95

Ala Arg Arg Gly Tyr Tyr Gly Pro Tyr Phe Asp Tyr Trp Gly Gln Gly
100 105 110

Thr Thr Leu Thr Val Ser Ser
115

<210> SEQ ID NO 8
<211> LENGTH: 113
<212> TYPE: PRT
<213> ORGANISM: Artificial sequence
<220> FEATURE:
<223> OTHER INFORMATION: the light chain variable region of the anti-Claudin 18.2 antibody

<400> SEQUENCE: 8

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asn Gly
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

```
Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Tyr Pro Tyr Thr Phe Gly Gly Gly Thr Lys Leu Glu Ile
            100                 105                 110

Lys


<210> SEQ ID NO 9
<211> LENGTH: 22
<212> TYPE: PRT
<213> ORGANISM: Artificial sequence
<220> FEATURE:
<223> OTHER INFORMATION: the amino acid sequence of the IgG kappa light
      chain signal peptide

<400> SEQUENCE: 9

Met Asp Met Arg Val Pro Ala Gln Leu Leu Gly Leu Leu Leu Leu Trp
1               5                   10                  15

Leu Arg Gly Ala Arg Cys
            20


<210> SEQ ID NO 10
<211> LENGTH: 66
<212> TYPE: DNA
<213> ORGANISM: Artificial sequence
<220> FEATURE:
<223> OTHER INFORMATION: the nucleotide sequence of the IgG kappa light
      chain signal peptide

<400> SEQUENCE: 10

atggatatga gggttcctgc acaactcctc ggtctgctgc tgctctggct gagaggagcc      60

agatgt                                                                 66


<210> SEQ ID NO 11
<211> LENGTH: 45
<212> TYPE: PRT
<213> ORGANISM: Artificial sequence
<220> FEATURE:
<223> OTHER INFORMATION: the amino acid sequence of the CD8 alpha hinge
      region

<400> SEQUENCE: 11

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 12
<211> LENGTH: 135
<212> TYPE: DNA
<213> ORGANISM: Artificial sequence
<220> FEATURE:
<223> OTHER INFORMATION: the nucleotide sequence of the CD8 alpha hinge
      region

<400> SEQUENCE: 12

accacgacgc cagcgccgcg accaccaaca ccggcgccca ccatcgcgtc gcagcccctg      60

tccctgcgcc cagaggcgtg ccggccagcg gcggggggcg cagtgcacac gagggggctg     120

gacttcgcct gtgat                                                      135
```

<210> SEQ ID NO 13
<211> LENGTH: 24
<212> TYPE: PRT
<213> ORGANISM: Artificial sequence
<220> FEATURE:
<223> OTHER INFORMATION: the amino acid sequence of the CD8 alpha transmembrane region

<400> SEQUENCE: 13

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 14
<211> LENGTH: 72
<212> TYPE: DNA
<213> ORGANISM: Artificial sequence
<220> FEATURE:
<223> OTHER INFORMATION: the nucleotide sequence of the CD8 alpha transmembrane region

<400> SEQUENCE: 14

```
atctacatct gggcgccctt ggccgggact tgtggggtcc ttctcctgtc actggttatc     60

accctttact gc                                                         72
```

<210> SEQ ID NO 15
<211> LENGTH: 42
<212> TYPE: PRT
<213> ORGANISM: Artificial sequence
<220> FEATURE:
<223> OTHER INFORMATION: the amino acid sequence of the 4-1BB intracellular co-stimulatory domain

<400> SEQUENCE: 15

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 16
<211> LENGTH: 126
<212> TYPE: DNA
<213> ORGANISM: Artificial sequence
<220> FEATURE:
<223> OTHER INFORMATION: the nucleotide sequence of the 4-1BB intracellular co-stimulatory domain

<400> SEQUENCE: 16

```
aagagaggca ggaagaagct gctgtacatc ttcaagcagc ccttcatgcg ccccgtgcag     60

acaacccagg aggaggacgg ctgcagctgt cggttcccag aggaggagga gggaggatgt    120

gagctg                                                               126
```

<210> SEQ ID NO 17
<211> LENGTH: 112
<212> TYPE: PRT
<213> ORGANISM: Artificial sequence
<220> FEATURE:
<223> OTHER INFORMATION: the amino acid sequence of the CD3 zeta signal transduction domain -continued

```
<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 18
<211> LENGTH: 336
<212> TYPE: DNA
<213> ORGANISM: Artificial sequence
<220> FEATURE:
<223> OTHER INFORMATION: the nucleotide sequence of the CD3 zeta signal
      transduction domain

<400> SEQUENCE: 18

agggtgaagt tttctcggag cgccgatgca ccagcatatc agcagggaca gaatcagctg      60

tacaacgagc tgaatctggg caggcgcgag gagtacgacg tgctggataa gcggagaggc     120

agagatcccg agatgggagg caagccaagg aggaagaacc ctcaggaggg cctgtataat     180

gagctgcaga aggacaagat ggccgaggcc tactctgaga tcggcatgaa gggagagcgg     240

agaaggggca agggacacga tggcctgtat cagggcctga gcacagccac caaggacacc     300

tacgatgcac tgcacatgca ggccctgcca cctagg                               336
```

ANTI-CLAUDIN18.2 ANTIGEN-BINDING FRAGMENT OR ANTIBODY, AND USE THEREOF18255119

CROSS-REFERENCE TO RELATED APPLICATIONS

This is a National Stage Application filed under 35 U.S.C. 371 based on International Patent Application No. PCT/CN2020/138240, filed on Dec. 22, 2020, which claims priority to Chinese Patent Application No. 202011486494.0, filed with the China National Intellectual Property Administration (CNIPA) on Dec. 16, 2020, the disclosures of which are incorporated herein by reference in their entireties.

TECHNICAL FIELD

The present application belongs to the field of biomedicines and in particular, relates to an anti-Claudin 18.2 antigen-binding fragment and antibody, and use thereof.

BACKGROUND

Tight junction is one of the forms of cell adhesion and is normally present in the junctional complexes in epithelial cells and endothelial cells. Tight junction molecules are composed of three types of whole membrane proteins including Occludin, Claudin proteins and junctional adhesion molecules and peripheral cytoplasmic proteins such as zonula occludens proteins. At present, it has been proven that Claudin proteins are important components of tight junctions of cells and establish the paracellular barrier that controls the flow of molecules between the cells. They have four transmembrane domains, with the $NH_2$-terminus and the COOH-terminus both located intracellularly. The abnormal expression of Claudin proteins may lead to structural destruction and functional damage of epithelial cells and endothelial cells, and thus Claudin proteins play an important role in the pathogenesis of various diseases.

Claudin-18 (CLDN18) belongs to the claudin family, and its encoding gene can form two subtypes of proteins: Claudin 18.1 (CLD18A1, GENBANK®: NM_016369) and Claudin 18.2 (CLD18A2, GENBANK®: NM_001002026) by alternative splicing. Claudin 18.1 is mainly expressed in normal lung tissues; Claudin 18.2, as a highly specific cell surface molecule, is only expressed on differentiated gastric epithelial cells (short-lived gastric epithelial cells) in normal tissues, but not on gastric stem cells. Claudin 18.2 is expressed in most of primary gastric cancers and their metastatic cancers, and the expression of such a target is present in 50%-80% of patients with gastric cancer. In addition, the activation and expression of Claudin 18.2 are often observed in pancreatic cancer, esophageal cancer, ovarian cancer and lung cancer. These characteristics indicate that Claudin 18.2 is an ideal drug target for tumor therapy.

Therefore, providing an antibody specifically binding to Claudin 18.2 has important therapeutic significance for cancer caused by Claudin 18.2-positive tumor cells.

SUMMARY

The present application provides an anti-Claudin 18.2 antigen-binding fragment and antibody, and use thereof. The antigen-binding fragment and antibody can specifically bind to Claudin 18.2 proteins, prepare the Claudin 18.2 proteins into chimeric antigen receptors and CAR-T cells, and have significant cytotoxicity on target cells expressing the Claudin 18.2 proteins.

In a first aspect, the present application provides an anti-Claudin 18.2 antigen-binding fragment including a heavy chain variable region and a light chain variable region;

- wherein the heavy chain variable region of the antigen-binding fragment includes CDR3, and CDR3 includes an amino acid sequence shown in SEQ ID NO. 3; and
- the light chain variable region of the antigen-binding fragment includes CDR3, and CDR3 includes an amino acid sequence shown in SEQ ID NO. 6.

In the present application, the antigen-binding fragment can specifically bind to Claudin 18.2, the antibody containing the antigen-binding fragment can specifically bind to a variety of sources of Claudin 18.2 proteins including human, murine, monkey and the like, and the antigen-binding fragment does not bind to Claudin 18.1. The antigen-binding fragment has a high specificity and is important for the research of drugs or vaccines targeting Claudin 18.2.

In some specific embodiments, the heavy chain variable region of the antigen-binding fragment further includes CDR1, and CDR1 includes an amino acid sequence shown in SEQ ID NO. 1.

In some specific embodiments, the light chain variable region of the antigen-binding fragment further includes CDR1, and CDR1 includes an amino acid sequence shown in SEQ ID NO. 4.

In some specific embodiments, the heavy chain variable region of the antigen-binding fragment further includes CDR2, and CDR2 includes an amino acid sequence shown in SEQ ID NO. 2.

In some specific embodiments, the light chain variable region of the antigen-binding fragment further includes CDR2, and CDR2 includes an amino acid sequence shown in SEQ ID NO. 5.

Corresponding sequences are shown in Table 1 below.

TABLE 1

| Antigen-binding fragment | SEQ ID NO. | Complementarity-determining region | Amino acid sequence |
|---|---|---|---|
| Heavy chain variable region | 1 | CDR1 | GYTFTSYVMH |
| | 2 | CDR2 | YINPYNDGTK |
| | 3 | CDR3 | RGYYGPYFDY |
| Light chain variable region | 4 | CDR1 | KSSQSLLNGGNQKNYLT |
| | 5 | CDR2 | WASTRES |
| | 6 | CDR3 | QNDYYYPYT |

In some specific embodiments, CDR1 of the heavy chain variable region of the antigen-binding fragment is an amino acid sequence shown in SEQ ID NO. 1, CDR2 is an amino acid sequence shown in SEQ ID NO. 2, and CDR3 is an amino acid sequence shown in SEQ ID NO. 3; CDR1 of the light chain variable region of the antigen-binding fragment is an amino acid sequence shown in SEQ ID NO. 4, CDR2 is an amino acid sequence shown in SEQ ID NO. 5, and CDR3 is an amino acid sequence shown in SEQ ID NO. 6.

In a second aspect, the present application provides an anti-Claudin 18.2 antibody including the antigen-binding fragment described in the first aspect.

In some specific embodiments, an amino acid sequence of a heavy chain variable region of the anti-Claudin 18.2 antibody is shown in SEQ ID NO. 7, and an amino acid sequence of a light chain variable region is shown in SEQ ID NO. 8.

The amino acid sequence of the heavy chain variable region (VH) of the antibody is as follows (SEQ ID NO. 7):

QVQLKQSGPELVKPGASVKMSCKASGYTFTSYVMHWVKQKPGQGLEWIGY

INPYNDGTKYNEKFKGKATLTSDKSSSTAYMELSSLTSEDSAVYYCARRG

YYGPYFDYWGQGTTLTVSS.

The amino acid sequence of the light chain variable region (VL) of the antibody is as follows (SEQ ID NO. 8):
DIVMTQSPSSLTVTAGEKVTMSCKSSQSLLNGGNQKNYLTWYQQKPGQP

PKLLIYWASTRESGVPDRFTGSGSGTDFTLTISSVQAEDLAVYYCQNDY

YYPYTFGGGTKLEIK.

The underlines in the preceding sequences are complementarity-determining regions.

Preferably, the anti-Claudin 18.2 antibody further includes a constant region.

Preferably, the anti-Claudin 18.2 antibody is modified with a glycosylation group.

The anti-Claudin 18.2 antibody may be present in the form of monomers or polymers. If the anti-Claudin 18.2 antibody is present in the form of polymers, one of its heavy chains and one of its light chains form an interchain disulfide bond, another heavy chain and another light chain form an interchain disulfide bond, and the former heavy chain and the later heavy chain form two interchain disulfide bonds.

Meanwhile, the present application further provides a method for preparing the anti-Claudin 18.2 antibody described in the second aspect, and the method specifically includes the following steps:

(1) BALB/c mice are immunized with DNA for hybridoma preparation, five BALB/C healthy female mice aged 7-8 weeks are selected for immunization, the immunized mice are detected for serologic titer after a certain immunization time, and the spleen cells of mice whose serologic titer reached the requirements of fusion experiment are fused with myeloma cells SP2/0 in an appropriate proportion under the action of a fusion agent to prepare hybridoma monoclonal cells;

(2) hybridoma cells are cultured in a selective medium R1640-HAT for 7-10 days and are cultured in an HT medium solution for 3-4 days, and the hybridoma supernatant samples are detected by ELISA on Day 1014 to obtain positive clones; and (3) flow screening experiment is carried out to subclone patent clones which bind to CLDN18.2 but not to CLDN18.1, and sequencing is carried out to obtain correct sequence clones.

In a third aspect, the present application provides a nucleic acid molecule including a DNA fragment for encoding the antigen-binding fragment described in the first aspect or the anti-Claudin 18.2 antibody described in the second aspect.

In a fourth aspect, the present application provides an expression vector including the nucleic acid molecule described in the third aspect.

In a fifth aspect, the present application provides a chimeric antigen receptor (CAR) including the anti-Claudin 18.2 antibody described in the second aspect.

In the present application, CAR-T cells containing the chimeric antigen receptor can highly express the anti-Claudin 18.2 antibody and has significant cytotoxicity on Claudin 18.2-positive cells.

Preferably, the chimeric antigen receptor further includes a signal peptide (Leader), a hinge region (Hinge), a transmembrane domain (TM), a co-stimulatory domain (ICD) and a signal transduction domain.

Preferably, the signal peptide includes a CD8α signal peptide and/or an IgGκ light chain signal peptide, and preferably is an IgGκ light chain signal peptide.

Preferably, the hinge region includes any one of a CD8α, CD28, human IgG1, IgG2, IgG4 or IgA hinge region, and preferably is a CD8α hinge region.

Preferably, the transmembrane domain includes a CD8α transmembrane region and/or a CD28 transmembrane region, and preferably is a CD8α transmembrane region.

Preferably, the signal conduction domain includes a CD3ζ signal conduction domain.

Preferably, the signal transduction domain further includes a co-stimulatory domain, for example, any one or a combination of at least two of 4-1BB, CD28 intracellular region, DAP10 or OX40.

In the present application, the chimeric antigen receptor targeting Claudin 18.2 includes an IgGκ light chain signal peptide, an anti-Claudin 18.2 antibody (scFv), a CD8α hinge region, a CD8α transmembrane region, 4-1BB and CD3ζ.

In the present application, the chimeric antigen receptor includes an IgGκ light chain signal peptide sequence, an antibody sequence (8D2-scFv) specifically binding to a Claudin 18.2 antigen, a CD8a hinge region sequence, a CD8α transmembrane region sequence, a 4-1BB co-stimulatory domain sequence and a CD3ζ signal transduction domain sequence.

The amino acid sequence of the IgGκ light chain signal peptide (SEQ ID NO. 9) is as follows:

MDMRVPAQLLGLLLLWLRGARC.

The amino acid sequence of the CD8α hinge region (hinge) (SEQ ID NO. 11) is as follows:

TTTPAPRPPTPAPTIASQPLSLRPEACRPAAGGAVHTRGLDFACD.

The amino acid sequence of the CD8α transmembrane region (TM) (SEQ ID NO. 13) is as follows:

IYIWAPLAGTCGVLLLSLVITLYC.

The amino acid sequence of the 4-1BB intracellular co-stimulatory domain (ICD) (SEQ ID NO. 15) is as follows:

KRGRKKLLYIFKQPFMRPVQTTQEEDGCSCRFPEEEEGGCEL.

The amino acid sequence of the CD3ζ signal transduction domain (SEQ ID NO. 17) is as follows:

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

In a sixth aspect, the present application provides a host cell including the nucleic acid molecule described in the third aspect, the expression vector described in the third aspect or the chimeric antigen receptor described in the fifth aspect.

In a seventh aspect, the present application provides a pharmaceutical composition including the anti-Claudin 18.2 antibody described in the second aspect.

Preferably, the pharmaceutical composition further includes an anti-tumor drug.

In the present application, the pharmaceutical compositions may also be used in combination with other anti-tumor drugs in a manner of simultaneous administration, separate administration or sequential administration.

Preferably, the pharmaceutical composition further includes any one or a combination of at least two of a pharmaceutically acceptable carrier, diluent or excipient.

In an eighth aspect, the present application provides use of the antigen-binding fragment described in the first aspect, the anti-Claudin 18.2 antibody described in the second aspect, the nucleic acid molecule described in the third aspect, the expression vector described in the fourth aspect, the chimeric antigen receptor described in the fifth aspect, the host cell described in the sixth aspect or the pharmaceutical composition described in the seventh aspect in the preparation of a cancer detection reagent and/or a cancer treatment drug.

Preferably, the cancer includes a Claudin 18.2-positive cancer.

Preferably, the cancer includes any one of gastric cancer, esophageal cancer, pancreatic cancer, lung cancer, ovarian cancer, colon cancer, liver cancer, head and neck cancer or gallbladder cancer.

Any numerical range described in the present application includes not only the above-listed point values but also any point values within the numerical range which are not listed. Due to the limitation of space and the consideration of simplicity, specific point values included in the range are not exhaustively listed in the present application.

Compared with the prior art, the present application has at least the beneficial effects described below.

(1) The antigen-binding fragment and anti-Claudin 18.2 antibody provided in the present application can specifically bind to a variety of species sources (including human, murine and cynomolgus monkey) of Claudin 18.2 proteins and have more choices in the selection of subsequent animal models; the EC50 value of the antibody binding to 293T-Hu18.2 is 2.303, the EC50 value of the antibody binding to 293T-Mu18.2 is 7.331, the EC50 value of the antibody binding to 293T-RM18.2 is 9.159, and the EC50 value of the antibody binding to MFC-Hu18.2 is 2.727 E-12; moreover, the antibody does not bind to 293T and murine MFC cells which stably express human Claudin 18.1, and through the membrane proteome array experiment, it can be seen that 8D2-scFv-hFc can specifically bind to Claudin 18.2 and does not bind to other non-target proteins, indicating that the anti-Claudin 18.2 antibody has significant specificity.

(2) The present application provides a chimeric antigen receptor 8D2 CAR. After the chimeric antigen receptor is transferred into T cells through lentivirus vectors, CAR-T cells expressing 8D2 CAR are obtained. The CAR-T cells have significant cytotoxicity on cells stably expressing Claudin 18.2 proteins and thus have a significant therapeutic value for Claudin 18.2-positive cancers such as gastric cancer, esophageal cancer, pancreatic cancer, lung cancer, ovarian cancer, colon cancer, liver cancer, head and neck cancer and gallbladder cancer.

BRIEF DESCRIPTION OF DRAWINGS

wherein FIG. 1*a* shows 293T-Hu18.1 cells, FIG. 1*b* shows MFC-Hu18.1 cells, FIG. 1*c* shows 293T-Hu18.2 cells, FIG. 1*d* shows MFC-Hu18.2 cells, FIG. 1*e* shows NCI-N87-Hu18.2 cells, Figure if shows MKN45-Hu18.2 cells, FIG. 1*g* shows 293T-Mu18.2 cells and FIG. 1*h* shows 293T-RM18.2 cells.

FIG. 2 (B) is a graph showing the detection results of the binding ability of the antibody 8D2 to murine MFC cell lines expressing different proteins in Example 3.

FIGS. 6*a* and 6*b* are graphs of flow cytometry detection results before and after T cells are infected by lentivirus in Example 5, wherein FIG. 6*a* shows results before infection and FIG. 6*b* shows results after infection.

DETAILED DESCRIPTION

Figure 1:
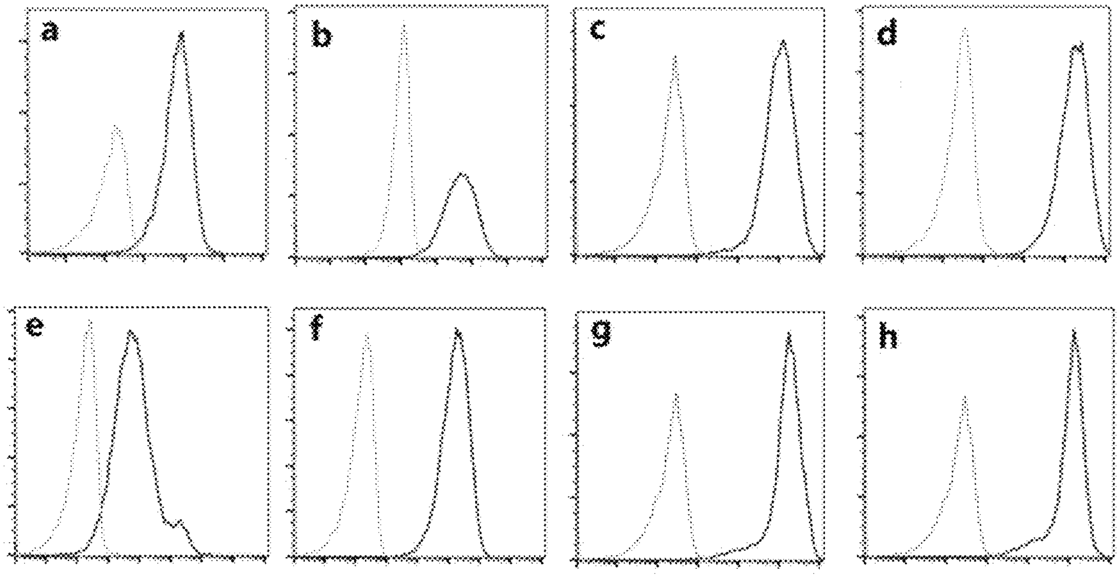
FIGS. 1*a*-1*h* are graphs of flow cytometry assay results of different cell lines constructed in Example 2.

Technical solutions of the present application are further described below through embodiments in conjunction with drawings. However, the following examples are simple examples of the present application and do not represent or limit the protection scope of the present application. The protection scope of the present application is subject to the claims.

In the following examples, unless otherwise specified, all reagents and consumables used are purchased from conventional reagent manufacturers in the art; and unless otherwise specified, the experimental methods and technical means used are conventional experimental methods and to technical means known in the art.

Example 1

In this example, BALB/c mice were immunized with DNA to prepare hybridoma monoclonal cells, hybridoma cells were cultured by using a selective culture medium R1640-HAT and then were cultured in an HT culture medium solution, and then hybridoma supernatant samples were detected by ELISA to obtain 99 positive clones;

subsequently, the flow screening experiment was carried out to subclone 7 parent clones (which bound to Claudin 18.2 and did not bind to Claudin 18.1) to obtain 6 subclones.

The correct sequence clone 8D2 was obtained by sequencing, that is, the anti-Claudin 18.2 antibody. After sequencing and identification, it is found that the sequence of the anti-Claudin 18.2 antibody 8D2 was as follows:

```
>8D2-VH (SEQ ID NO. 7):
QVQLKQSGPELVKPGASVKMSCKASGYTFTSYVMHWVKQKPGQGLEWIGY
INPYNDGTKYNEKFKGKATLTSDKSSSTAYMELSSLTSEDSAVYYCARRG
YYGPYFDYWGQGTTLTVSS;
>8D2-VL (SEQ ID NO. 8):
DIVMTQSPSSLTVTAGEKVTMSCKSSQSLLNGGNQKNYLTWYQQKPGQPP
KLLIYWASTRESGVPDRFTGSGSGTDFTLTISSVQAEDLAVYYCQNDYYY
PYTFGGGTKLEIK.
```

Example 2

In this example, the construction of cell lines stably expressing Claudin 18.2 proteins was detected by flow cytometry, and the steps were as follows.

(1) Construction of Expression Vectors of Claudin 18.1 and Claudin 18.2 and Preparation of Lentivirus The complete coding sequence of human Claudin 18.1 (GENBANK®: NM 016369, referred to as "Hu18.1" hereinafter), the complete coding sequence of human Claudin 18.2 (GENBANK®: NM_001002026, referred to as "Hu18.2" hereinafter), the complete coding sequence of murine Claudin 18.2 (GENBANK®: NM_001194921.1, referred to as "Mu18.2" hereinafter) and the complete coding sequence of monkey Claudin 18.2 (GENBANK®: XM_001114708.4, referred to as "RM18.2" hereinafter) were synthesized by the complete series of PCR-based gene synthesis technology;

after enzyme digestion, ligation and transformation, the clones were selected for PCR identification and sequencing to confirm that the correct lentivirus vector plasmids pCDH-Claudin 18.1 and pCDH-Claudin 18.2 were obtained;

the above plasmids were co-transfected into 293T cells with gag/pol, Rev and VSV-G vectors which were required for a four-plasmid system to package lentivirus vectors, respectively; after 72 h of transfection, Claudin 18.1 and Claudin 18.2 virus solutions were collected, concentrated, subpackaged and stored at −80° C.

(2) Construction of Claudin 18.1 and Claudin 18.2 Exogenous Stable Expression Lines and Flow Assay The collected Claudin 18.1 and Claudin 18.2 virus solutions were added to 293T cells and mouse gastric cancer cells MFC (purchased from NANJING CO-BIOER, CBP60882) spread in T75 cell culture flasks, respectively;

in addition, human gastric cancer cells NCI-N87 (purchased from NANJING CO-BIOER, CBP60491) and human gastric cancer cells MKN45 (purchased from NANJING CO-BIOER, CBP60488) were infected with the Claudin 18.2 virus solution for constructing 293T-Hu18.1, MFC-Hu18.1, 293T-Hu18.2, MFC-Hu18.2, NCI-N87-Hu18.2, MKN45-Hu18.2, 293T-Mu18.2 and 293T-RM18.2 cell lines, respectively. Specific information is shown in Table 2 below.

TABLE 2

| No. | Cell line | Expression protein | Host cell |
|---|---|---|---|
| 1 | 293T-Hu18.1 | Hu18.1 | 293T cell |
| 2 | MFC-Hu18.1 | Hu18.1 | Mouse gastric cancer cell MFC |
| 3 | 293T-Hu18.2 | Hu18.2 | 293T cell |
| 4 | MFC-Hu18.2 | Hu18.2 | Mouse gastric cancer cell MFC |

TABLE 2-continued

| No. | Cell line | Expression protein | Host cell |
|---|---|---|---|
| 5 | NCI-N87-Hu18.2 | Hu18.2 | Human gastric cancer cell NCI-N87 |
| 6 | MKN45-Hu18.2 | Hu18.2 | Human gastric cancer cell MKN45 |
| 7 | 293T-Mu18.2 | Mu18.2 | 293T cell |
| 8 | 293T-RM18.2 | RM18.2 | 293T cell |

After continuous screening and culture with puromycin, the construction of the above cell lines was detected by flow antibodies, and the results are as shown in FIG. 1. As can be seen from the figure, 293T-Hu18.1 (FIG. 1*a*), MFC-Hu18.1 (FIG. 1*b*), 293T-Hu18.2 (FIG. 1*c*), MFC-Hu18.2 (FIG. 1*d*), NCI-N87-Hu18.2 (FIG. 1*e*), MKN45-Hu18.2 (FIG. 10, 293T-Mu18.2 (FIG. 1*g*) and 293T-RM18.2 (FIG. 1*h*) cell lines were successfully constructed in this example.

Example 3

In this example, the binding ability of the antibody 8D2 to each cell line was analyzed by a flow cytometer (BECKMAN COULTER, CytoFLEX S Flow Cytometer).

The specific method is as follows:

293T-Hu18.1, MFC-Hu18.1, 293T-Hu18.2, MFC-Hu18.2, NCI-N87-Hu18.2, MKN45-Hu18.2, 293T-Mu18.2 and 293T-RM18.2 tumor cells in the logarithmic growth phase were inoculated into 6 cm plates, with the inoculated cell density of 90%, and cultured in an incubator at 37° C. overnight;

the cells were digested with trypsin and collected by centrifugation at 200 g×5 min;

the cells were resuspended at the concentration of $1\times10^6$/mL in phosphate buffer (NBS PBS) containing 1% calf serum by mass and then added to flow-special tubes at the rate of 100 μL/tube;

the cells were centrifuged at 200 g×5 min, the supernatant was discarded, and the antibody 8D2 to be tested was added, with 8K13 as an isotype control, where the final concentration of the antibody was 25, 5, 1 and 0.2 μg/mL, and 100 μL was added to each tube;

the cells were incubated at room temperature for 30 min, the supernatant was discarded, 1:20 diluted FITC fluorescent-labeled goat anti-human secondary antibody (BioLegend, Cat. No. 409306) was added, with 100 μL to each tube, and the cells were incubated at room temperature for 30 min;

the supernatant was discarded, the cells were resuspended in 200 μL of 1% NBS PBS and detected by flow cytometry, and then the data were analyzed by flow cytometry data analysis software Flowjo 10.

Flow cytometry analysis showed that the antibody 8D2 could specifically recognize 293T, MKN45, NCI-N87 and murine MFC cells stably expressing human Claudin 18.2 and did not bind to 293T and murine MFC cells stably expressing human Claudin 18.1; therefore, the 8D2 antibody could specifically recognize human Claudin 18.2 proteins; meanwhile, the antibody 8D2 could also bind to cells stably expressing murine and monkey Claudin 18.2, indicating that the antibody 8D2 could also specifically recognize murine and monkey Claudin 18.2.

Figure 2A:
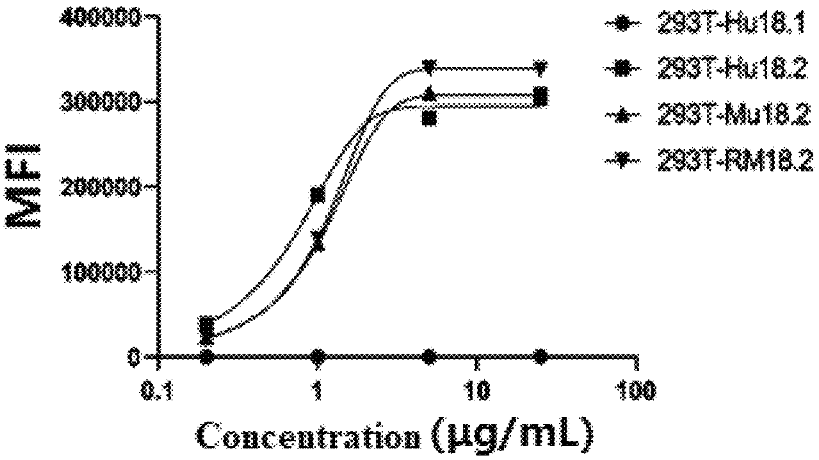
FIG. 2 (A) is a graph showing the detection results of the binding ability of the antibody 8D2 to 293T cell lines expressing different proteins in Example 3.
Figure 2B:
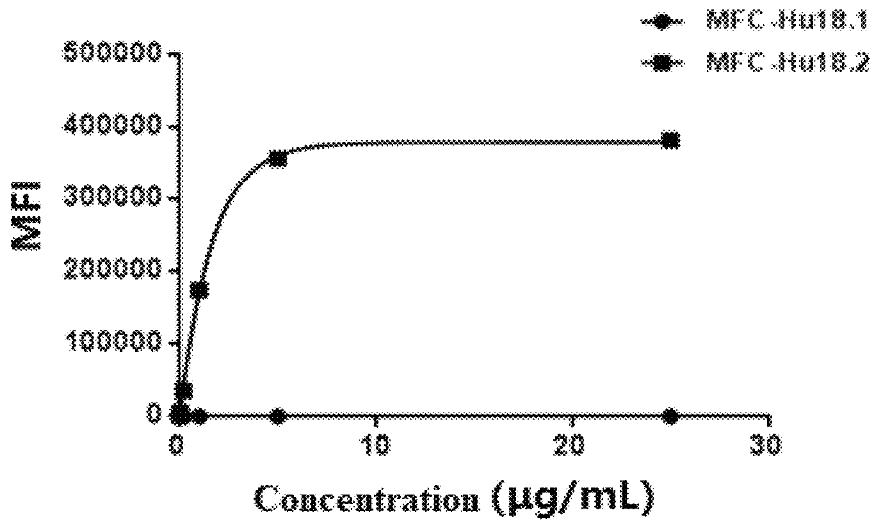

Some flow cytometry analysis results are shown in FIG. 2 (A) and FIG. 2 (B).

As shown in FIG. 2 (A), the EC50 value of the antibody 8D2 binding to 293T-Hu18.2 was 2.303, the EC50 value of the antibody 8D2 binding to 293T-Mu18.2 was 7.331, the EC50 value of the antibody 8D2 binding to 293T-RM18.2 was 9.159, and the antibody 8D2 basically did not bind to 293T-Hu18.1.

As shown in FIG. 2 (B), the antibody 8D2 basically did not bind to MFC-Hu18.1, and the EC50 value of the antibody 8D2 binding to MFC-Hu18.2 was 2.727 E-12.

Example 4

In this example, an anti-Claudin 18.2 chimeric antigen receptor (8D2 CAR) and its expression vector were constructed.

(1) Sequence Design

The chimeric antigen receptor included an IgGκ light chain signal peptide sequence (Leader), an antibody sequence (8D2-scFv) specifically binding to a Claudin 18.2 antigen, a CD8α hinge region sequence (Hinge), a CD8α transmembrane region sequence, a 4-1BB co-stimulatory domain sequence and a CD3ζ signal transduction domain sequence.

Figure 3:
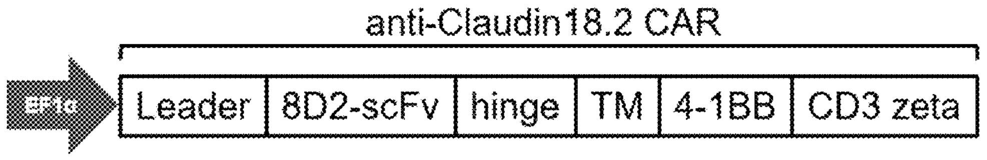
FIG. 3 is a structure diagram of a chimeric antigen receptor constructed in Example 4.

The specific structure is shown in FIG. 3, and the amino acid sequences and nucleotide sequences of each part are shown in Table 3 below.

TABLE 3

| Name | SEQ ID NO. | Amino acid sequence and nucleotide sequence |
|---|---|---|
| IgGκ light chain signal peptide | 9 | MDMRVPAQLLGLLLLWLRGARC |
| | 10 | ATGGATATGAGGGTTCCTGCACAACTCCTCGGTCTGCTGCTGCTCTGGCTGAGAGGAGCCAGATGT |
| CD8a hinge region | 11 | TTTPAPRPPTPAPTIASQPLSLRPEACRPAAGGAVHTRGLDFACD |
| | 12 | ACCACGACGCCAGCGCCGCGACCACCAACACCGGCGCCCACCATCGCGTCGCAGCCCCTGTCCCTGCGCCCAGAGGCGTGCCGGCCAGCGGCGGGGGGCGCAGTGCACACGAGGGGGCTGGACTTCGCCTGTGAT |
| CD8a transmembrane region | 13 | IYIWAPLAGTCGVLLLSLVITLYC |
| | 14 | ATCTACATCTGGGCGCCCTTGGCCGGGACTTGTGGGGTCCTTCTCCTGTCACTGGTTATCACCCTTTACTGC |
| 4-1BB costimulatory domain | 15 | KRGRKKLLYIFKQPFMRPVQTTQEEDGCSCRFPEEEEGGCEL |
| | 16 | AAGAGAGGCAGGAAGAAGCTGCTGTACATCTTCAAGCAGCCCTTCATGCGCCCCGTGCAGACAACCCAGGAGGAGGACGGCTGCAGCTGTCGGTTCCCAGAGGAGGAGGAGGGAGGATGTGAGCTG |
| CD3ζ signal transduction domain | 17 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| | 18 | AGGGTGAAGTTTTCTCGGAGCGCCGATGCACCAGCATATCAGCAGGGACAGAATCAGCTGTACAACGAGCTGAATCTGGGCAGGCGCGAGGAGTACGACGTGCTGGATAAGCGGAGAGGCAGAGATCCCGAGATGGGAGGCAAGCCAAGGAGGAAGAACCCTCAGGAGGGCCTGTATAATGAGCTGCAGAAGGACAAGATGGCCGAGGCCTACTCTGAGATCGGCATGAAGGGAGAGCGGAGAAGGGGCAAGGGACACGATGGCCTGTATCAGGGCCTGAGCACAGCCACCAAGGACACCTACGATGCACTGCACATGCAGGCCCTGCCACCTAGG |

(2) Construction of an Anti-Claudin 18.2 Chimeric Antigen Receptor Expression Vector First, the 8D2 CAR sequence was synthesized by gene synthesis, and the 8D2 CAR synthesized by gene synthesis and empty vectors were double digested with EcoRI and BamHI. After 30 min of digestion in a water bath at 37° C., DNA electrophoresis was carried out with 1.5% agarose gel, and then the 8D2 CAR and the empty vectors were purified and recovered with an agarose gel kit from TIANGEN;

then, the pCDH-EF1 vectors were ligated to the 8D2 CAR gene fragments, and the specific connection system is shown in Table 4 below:

TABLE 4

Figure 4:
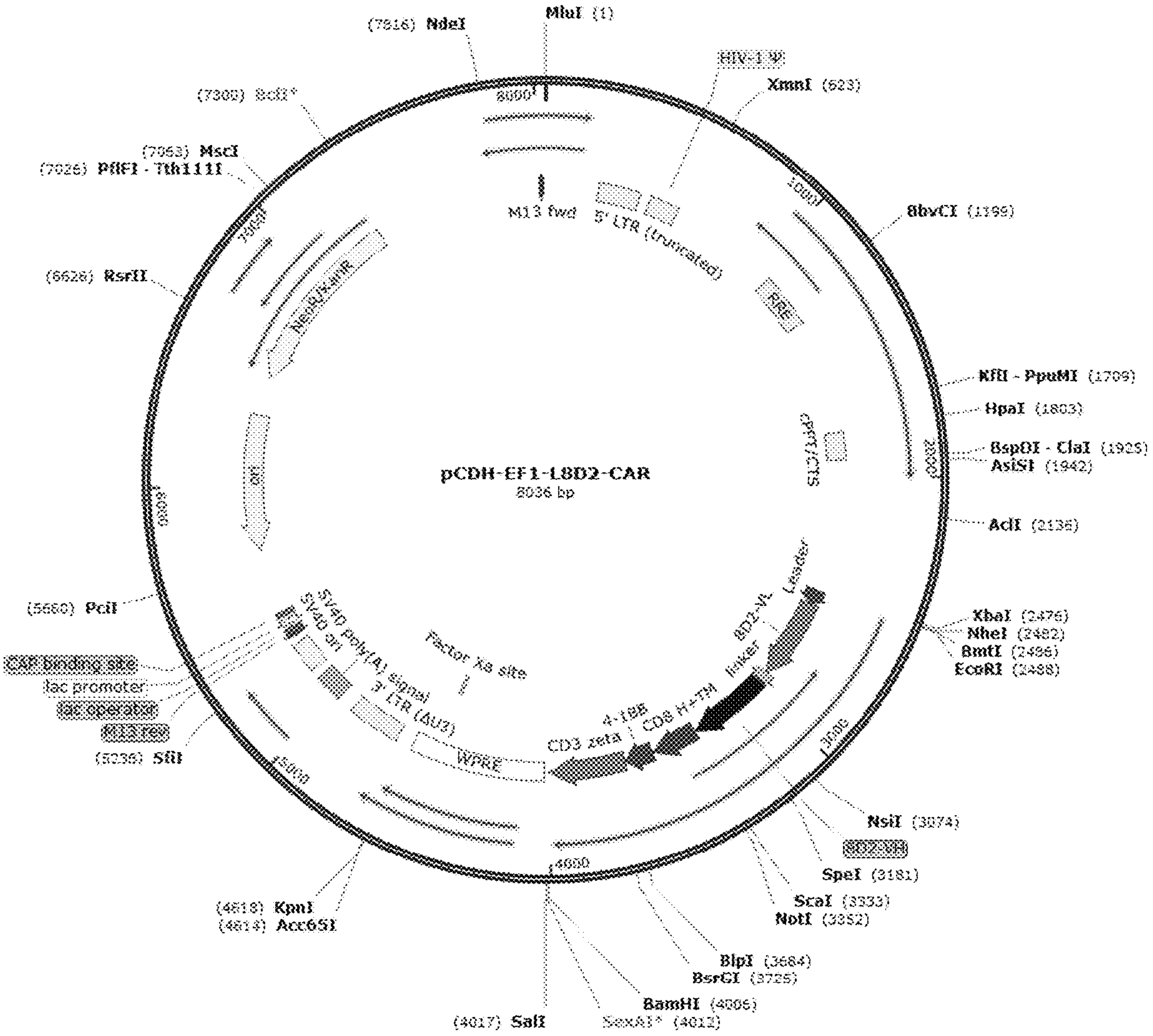
FIG. 4 is a map of a lentivirus expression vector expressing the chimeric antigen receptor in Example 4.
Figure 5:
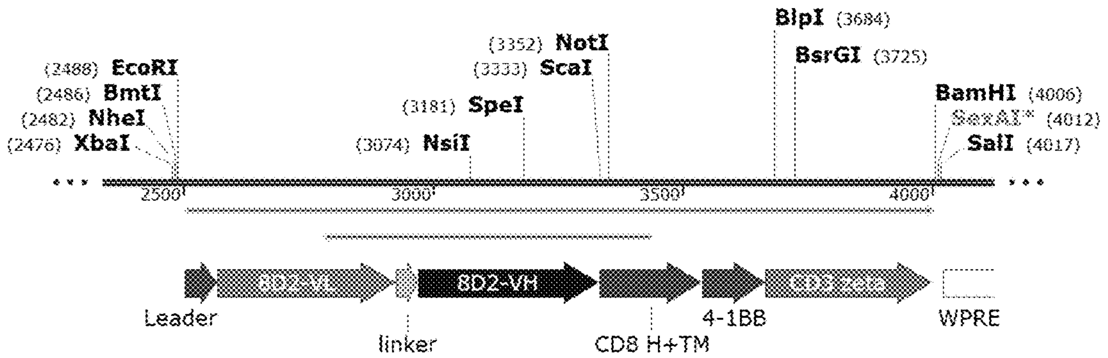
FIG. 5 is a map of a chimeric antigen receptor in the lentivirus expression vector in Example 4.

| Reagent | Dosage |
|---|---|
| pCDH-EF1 vector | 2 μL (50 ng) |
| 8D2 CAR gene | 10 μL (150 ng) |
| T4 DNA Ligase Buffer | 2 μL |
| T4 DNA Ligase (NEB) | 1 μL |
| $ddH_2O$ | 5 μL |
| Total | 20 μL |

the ligation was carried out at 22° C. for 1 h, the ligated products were directly transformed into Stbl3 *Escherichia coli* competent cells. 200 μL of the transformed products were coated on an ampicillin-resistant LB plate, and the LB plate was cultured in an incubator at 37° C. overnight;

the next morning, three monoclones were randomly selected for colony PCR identification, and the positive clones were sampled and sequenced to obtain the anti-Claudin 18.2 chimeric antigen receptor lentivirus expression plasmid, that is, pCDH-EF1-L8D2-CAR. The vector map of Claudin 18.2 is shown in FIG. 4, and the sequence of the chimeric antigen receptor is shown in FIG. 5.

Example 5

In this example, the lentivirus expression vector was packaged with lentivirus, CAR-T cells were constructed, and the infection efficiency of lentivirus to T cells was detected.

(1) Lentivirus Packaging with a Four-Plasmid System

The four-plasmid system expressed gag/pol, Rev and VSV-G which were required for lentivirus vector packaging as well as an artificial chimeric antigen receptor composed of engineered stable single-chain antibodies, respectively. The four plasmids were transfected into 293T cells instantaneously, with a total mass of 10 μg;

the plasmids were added into serum-free DMEM, mixed and placed for 15 min, and then the mixture was added to a T75 culture flask spread with 293T cells, gently mixed and cultured in a 5% $CO_2$ cell incubator at 37° C. for 6 h;

after 6 h, a fresh culture medium was replaced for continued culture, and 10 mM of sodium butyrate solution was added; after 72 h, the culture supernatant of lentivirus was collected for purification and detection.

(2) Amplification of CAR-T Cells 30 mL of whole blood was collected, peripheral blood was diluted with normal saline at 1:1, Ficoll was added to a centrifuge tube, the diluted peripheral blood was slowly added to the centrifuge tube and centrifuged at 1500 rpm for 30 min, and the PBMC layer was gently pipetted into another centrifuge tube;

the PBMC was washed with normal saline several times and then transferred into a CAR-T cell medium (containing 50 ng/mL OKT3 and 300 IU/mL IL-2) for culture;

after the PBMC was isolated, the PBMC needed to be activated with the CAR-T cell medium containing 50 ng/mL OKT3 and 300 IU/mL IL-2;

after 2 days, the medium was replaced with a CAR-T cell medium containing 300 IU/mL for expanded culture;

then, the cells were counted every two days, the CAR-T cell culture medium containing 300 IU/mL was also replaced every two days, the cell concentration was maintained at $0.5\times10^6$-$1\times10^6$/mL, and the cells were observed continuously for 10 days.

(3) Infection of T Cells with Lentivirus

The infection efficiency of lentivirus to T cells was improved using RetroNectin, and 30 μg of RetroNectin was coated in a 6-well plate and placed in a cell incubator at 37° C. for 2 h;

RetroNectin was absorbed, and the coated 6-well plate was sealed with the Hank's solution containing 2.5% BSA and placed in a cell incubator at 37° C. for 0.5 h;

the sealant was absorbed, the 6-well plate was washed with the Hank's solution containing 2% Hepes, an X-VIVO medium was added, an appropriate amount of lentivirus solution was added, and the mixture was centrifuged at 2000 g for 2 h;

the supernatant was discarded, $1\times10^6$ T cells were added, centrifuged at 1000 g for 10 min and cultured in a 5% $CO_2$ cell incubator at 37° C., and the above procedure was repeated on the second day; the expression of 8D2 CAR was determined 5 days after infection, 8D2 CAR bound to FITC-Protein L, and the expression of 8D2 CAR was detected by flow cytometry.

Figure 6:
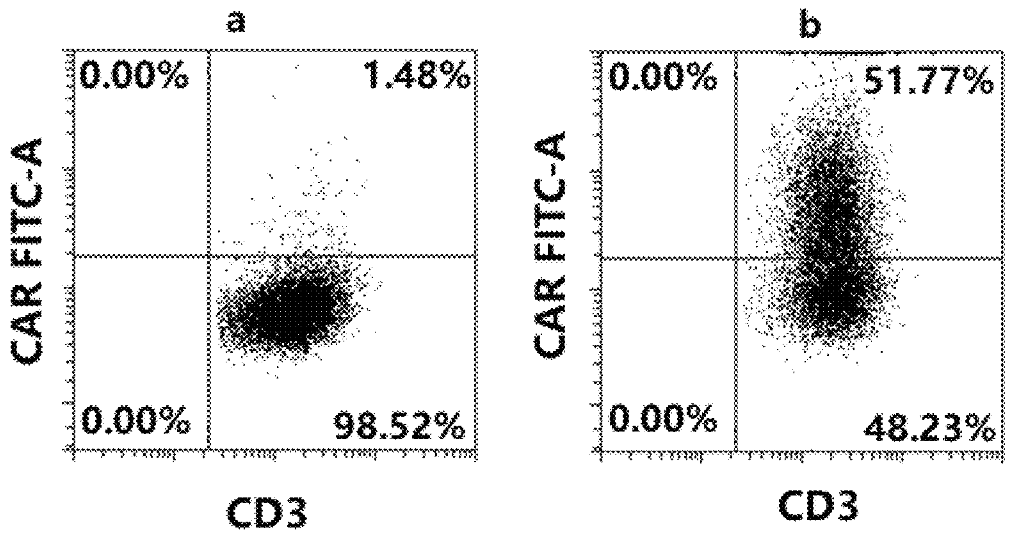

The results are shown in FIG. 6. The results showed that the positive rate of CD3 before infection was 98.52% (FIG. 6*a*), and the expression positive rate of 8D2 CAR was 51.77% (FIG. 6*b*).

Example 6

In this example, a cytotoxicity assay was carried out using 8D2 CAR, with the blank control NC (untransfected T cells) as a control.

The cytotoxicity of CAR-T cells to 293T-Hu18.1 cells (293T cells stably expressing human Claudin 18.1), 293T-Hu18.2 cells (293T cells stably expressing human Claudin 18.2) and 293T-Mu18.2 cells (293T cells stably expressing murine Claudin 18.2) cells was measured by LDH.

The detection method adopted in this example was carried out with reference to the detection method described in CN104877032A and included the following steps.

The cells were centrifuged, washed with a serum-free phenol red-free DMEM medium and then counted.

$1\times10^6$ 293T-Hu18.1, 293T-Hu18.2 and 293T-Mu18.2 cells were taken in 50 μL each and spread in a 96-well plate as target cells.

Untransfected T cells and each CAR-T cells were added according to the ratio of target cell:effector cell=1:1/4/8.

The cells were cultured at 37° C., 5% $CO_2$ and a certain humidity for 12 h. The lysate was added as a positive control, and then the mixture was centrifuged at 250 g for 5 min. 100 μL of culture supernatant was taken from each well and added to a new 96-well plate, 20 μL of reaction solution was added, and the mixture reacted in a darkroom for 2030 min and detected with a microplate reader at 590 nm.

The dissolution percentage was calculated according to the following formula:

cytotoxicity (%)=[(experimental wells-medium background wells)−(effector cell spontaneous LDH release wells-medium background wells)−(target cell spontaneous LDH release wells-medium background wells)]/[(target cell maximum LDH release wells-volume correction wells)−(target cell spontaneous LDH release wells-medium background wells)]×100%.

Figure 7:
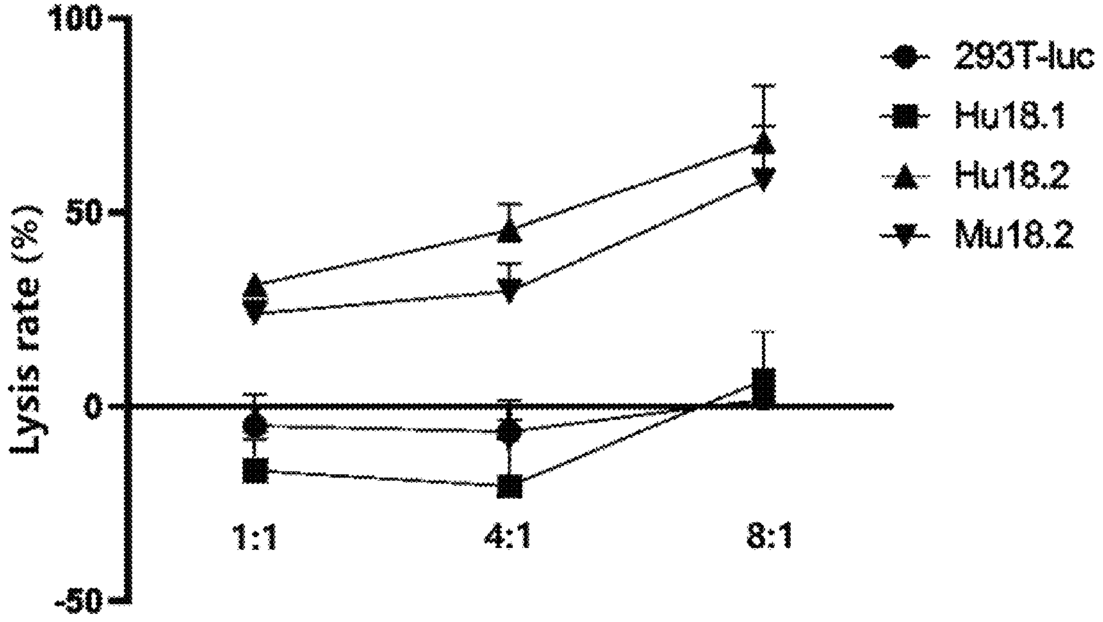
FIG. 7 is a graph of the detection results of the killing ability of the 8D2 CAR-T cells to target cells under different effector-target ratios in Example 6.

The results are shown in FIG. 7. 8D2 CAR-T cells could specifically kill 293T cells stably expressing human Claudin 18.2 (293T-Hu18.2) and 293T cells stably expressing murine Claudin 18.2 (293T-Mu18.2) and had no killing ability to 293T cells stably expressing human Claudin 18.1 (293T-Hu18.1).

Example 7

In this example, the non-target binding interaction of the antibody was verified using a Membrane Proteome Array.

First, the antibody fusion protein 8D2-scFv-hFc was expressed, and 8D2-scFv-hFc was the Fc segment of a single-chain antibody sequence of 8D2 fused with human IgG1; the membrane proteome array (MPA) was a platform for analyzing the targeting of specific antibodies and other ligands to human membrane proteins and could be used to determine the specificity of antibody targets.

Plasmids containing approximately 6000 membrane protein clones (94% or more of the human membrane protein group) were transfected into HEK-293T cells (ATCC, CRL-3216), respectively or to QT6 cells (ATCC, CRL-1708) in a 384-well cell culture plate (Corning, 3764), 18,000 cells/well.

After 36 h of incubation, the test antibody was added to the membrane proteome array matrix plate at a predetermined concentration, and the binding of the antibody 8D2-scFv-hFc to about 6000 types of membrane protein expression cells was directly detected by flow cytometry. Therefore, all target proteins had a native state and an appropriate post-translational modification.

Figure 8:
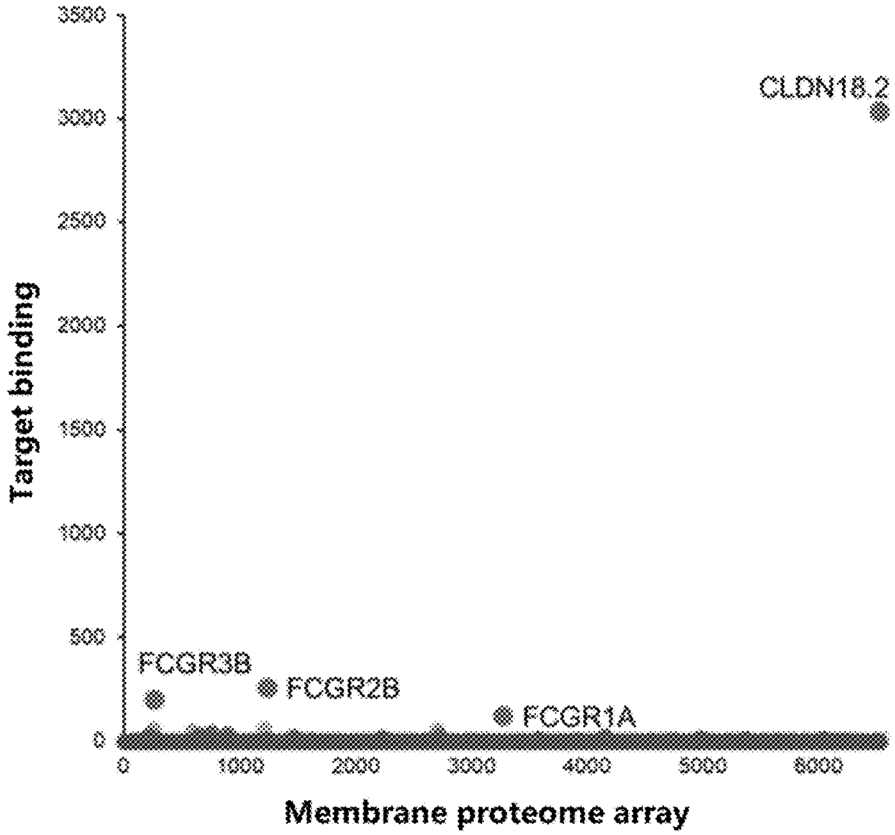
FIG. 8 is a graph the results of the specific interaction of 8D2-scFv-hFc antibodies verified with a membrane proteome array in Example 7.

The membrane proteome array results are shown in FIG. 8: 8D2-scFv-hFc could specifically bind to human Claudin 18.2 and did not bind to other non-target proteins, where FCGR1A, FCGR2B, and FCGR3B were IgG Fc receptors.

In conclusion, the anti-Claudin 18.2 antibody provided by the present application can specifically bind to a variety of sources of Claudin 18.2 proteins, including human, murine and monkey ones, basically has no binding ability to other proteins and has a high specificity; meanwhile, the CAR provided herein and the T cell containing the CAR have significant cytotoxicity to cells expressing the Claudin 18.2 protein; therefore, the anti-Claudin 18.2 antibody provided herein has a specific therapeutic effect on diseases targeting the Claudin 18.2 protein.

The applicant states that the above are only the embodiments of the present application and are not intended to limit the protection scope of the present application. Those skilled in the art should understand that any changes or substitutions easily conceivable by those skilled in the art within the technical scope disclosed in the present application fall within the protection scope and the disclosed scope of the present application.

What is claimed is:

1. An anti-Claudin 18.2 antigen-binding fragment, comprising a heavy chain variable region and a light chain variable region, wherein the heavy chain variable region comprises complementarity-determining region 1 (CDR1) comprising the amino acid sequence of SEQ ID NO: 1, CDR2 comprising the amino acid sequence of SEQ ID NO: 2, and CDR3 comprising the amino acid sequence of SEQ ID NO: 3; and wherein the light chain variable region comprises complementarity-determining region 1 (CDR1) comprising the amino acid sequence of SEQ ID NO: 4, CDR2 comprising the amino acid sequence of SEQ ID NO: 5, and CDR3 comprising the amino acid sequence of SEQ ID NO: 6.

2. An anti-Claudin 18.2 antibody, comprising the antigen-binding fragment according to claim 1;

optionally, the anti-Claudin 18.2 antibody comprises a heavy chain variable region comprising the amino acid sequence of SEQ ID NO: 7, and a light chain variable region comprising the amino acid sequence of SEQ ID NO: 8; and/or optionally, the anti-Claudin 18.2 antibody is modified with a glycosylation group.

3. A pharmaceutical composition, comprising the anti-Claudin 18.2 antibody according to claim 2;

optionally, the pharmaceutical composition further comprises an anti-tumor drug; and/or optionally, the pharmaceutical composition further comprises any one or a combination of at least two of a pharmaceutically acceptable carrier, diluent or excipient.

4. A chimeric antigen receptor, comprising the anti-Claudin 18.2 antibody according to claim 2.

5. The chimeric antigen receptor according to claim 4, wherein the chimeric antigen receptor further comprises a signal peptide, a hinge region, a transmembrane domain and a signal transduction domain;

wherein the signal peptide comprises a CD8α signal peptide or an IgGκ light chain signal peptide;

wherein the hinge region comprises the hinge region of CD8α, CD28, IgG1, IgG2, IgG4 or IgA;

wherein the transmembrane domain comprises a CD8α transmembrane domain or a CD28 transmembrane domain; and wherein the signal conduction domain comprises a CD3ζ signal conduction domain.

6. A nucleic acid molecule, comprising a DNA fragment encoding the antigen-binding fragment according to claim 1.

7. An expression vector, comprising the nucleic acid molecule according to claim 6.

8. A host cell, comprising the nucleic acid molecule according to claim 6.

9. A method for treating a Claudin 18.2-positive cancer comprising administering an effective amount of the antigen-binding fragment according to claim 1 to a subject in need thereof.

10. The method according to claim 9, wherein the Claudin 18.2-positive cancer is gastric cancer, esophageal cancer, pancreatic cancer, lung cancer, ovarian cancer, colon cancer, liver cancer, head and neck cancer, or gallbladder cancer.

* * * * *